(12) United States Patent
Wen et al.

(10) Patent No.: US 8,785,597 B2
(45) Date of Patent: Jul. 22, 2014

(54) MUTANT G-CSF FUSION PROTEIN, AND PREPARATION AND USE THEREOF

(75) Inventors: Xiaofang Wen, China Medicine (CN); Yiliang Wu, China Medicine (CN); Yefei Wang, China Medicine (CN); Zhiyu Yang, China Medicine (CN); Min Fan, China Medicine (CN); Yujiao Wang, China Medicine (CN); Xiaochun Fang, China Medicine (CN); You Lu, China Medicine (CN)

(73) Assignee: Jiangsu T-Mab Biopharma Co., Ltd., Jiangsu Province (CN)

( * ) Notice: Subject to any disclaimer, the term of this patent is extended or adjusted under 35 U.S.C. 154(b) by 0 days.

(21) Appl. No.: 13/575,752

(22) PCT Filed: Jun. 30, 2010

(86) PCT No.: PCT/CN2010/074817
§ 371 (c)(1),
(2), (4) Date: Jul. 27, 2012

(87) PCT Pub. No.: WO2012/000187
PCT Pub. Date: Jan. 5, 2012

(65) Prior Publication Data
US 2013/0164251 A1    Jun. 27, 2013

(51) Int. Cl.
*C07K 1/00* (2006.01)
*C12P 21/04* (2006.01)
*C12N 15/00* (2006.01)
*C12N 5/00* (2006.01)
*A61K 38/18* (2006.01)

(52) U.S. Cl.
USPC ....... 530/350; 435/69.7; 435/320.1; 435/325; 514/7.6

(58) Field of Classification Search
None
See application file for complete search history.

(56) References Cited

PUBLICATIONS

Ngo et al. (1994), The Protein Folding Problem an Tertiary Structure Prediction, pp. 492-495.*
Wells, (1990), Biochemistry, vol. 26, No. 37, pp. 8509-8517.*

* cited by examiner

*Primary Examiner* — Christine J Saoud
*Assistant Examiner* — Jegatheesan Seharaseyon
(74) *Attorney, Agent, or Firm* — Ming Chow; Sinorica, LLC (57) ABSTRACT

The present invention relates to a mutant G-CSF fusion protein. The mutant G-CSF fusion protein is a fusion protein having the activity of stimulating the proliferation of neutrophilic granulocytes, and having a basic structure of G-CSF/carrier protein or carrier protein/G-CSF; wherein the G-CSF moiety comprises multipoint substitutions thus resulting in changes in biological activity and binding affinity. Compared with existing products, the mutant G-CSF fusion protein in the present invention has longer half-life and higher biological activity. Administration of the pharmaceutical preparation containing this mutant G-CSF fusion protein could be used in the treating neutropenia.

16 Claims, 4 Drawing Sheets

```
                            SEQUENCE LISTING

<160> NUMBER OF SEQ ID NOS: 6

<210> SEQ ID NO 1
<211> LENGTH: 174
<212> TYPE: PRT
<213> ORGANISM: Homo sapiens

<400> SEQUENCE: 1

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
<211> LENGTH: 174
<212> TYPE: PRT
<213> ORGANISM: Artificial Sequence
<220> FEATURE:
<223> OTHER INFORMATION: Amino acid sequence of mG-CSF which contains
      T1A, L3T, G4Y, P5R, K34H, L35I, K40H, and L41I substitutions

<400> SEQUENCE: 2

Ala Pro Thr Tyr Arg Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu His Ile Cys Ala Thr Tyr His Ile Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
```

```
                     85                  90                  95
Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 3
<211> LENGTH: 783
<212> TYPE: PRT
<213> ORGANISM: Artificial Sequence
<220> FEATURE:
<223> OTHER INFORMATION: signal peptide of human serum albumin

<400> SEQUENCE: 3

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
```

-continued

```
                275                 280                 285
Cys Glu Asn Gln Asp Ser Ile Ser Ser Lys Leu Lys Glu Cys Cys Glu
290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
                340                 345                 350
Met Phe Leu Tyr Glu Tyr Ala Arg Arg His Pro Asp Tyr Ser Val Val
                355                 360                 365
Leu Leu Leu Arg Leu Ala Lys Thr Tyr Glu Thr Thr Leu Glu Lys Cys
                370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
                420                 425                 430
Val Arg Tyr Thr Lys Lys Val Pro Gln Val Ser Thr Pro Thr Leu Val
                435                 440                 445
Glu Val Ser Arg Asn Leu Gly Lys Val Gly Ser Lys Cys Cys Lys His
                450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
                500                 505                 510
Ser Ala Leu Glu Val Asp Glu Thr Tyr Val Pro Lys Glu Phe Asn Ala
                515                 520                 525
Glu Thr Phe Thr Phe His Ala Asp Ile Cys Thr Leu Ser Glu Lys Glu
                530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
                580                 585                 590
Ala Glu Glu Gly Lys Lys Leu Val Ala Ala Ser Gln Ala Ala Leu Gly
                595                 600                 605
Leu Thr Pro Leu Gly Pro Ala Ser Ser Leu Pro Gln Ser Phe Leu Leu
                610                 615                 620
Lys Cys Leu Glu Gln Val Arg Lys Ile Gln Gly Asp Gly Ala Ala Leu
625                 630                 635                 640
Gln Glu Lys Leu Cys Ala Thr Tyr Lys Leu Cys His Pro Glu Glu Leu
                645                 650                 655
Val Leu Leu Gly His Ser Leu Gly Ile Pro Trp Ala Pro Leu Ser Ser
                660                 665                 670
Cys Pro Ser Gln Ala Leu Gln Leu Ala Gly Cys Leu Ser Gln Leu His
                675                 680                 685
Ser Gly Leu Phe Leu Tyr Gln Gly Leu Leu Gln Ala Leu Glu Gly Ile
                690                 695                 700
```

```
Ser Pro Glu Leu Gly Pro Thr Leu Asp Thr Leu Gln Leu Asp Val Ala
705                 710                 715                 720

Asp Phe Ala Thr Thr Ile Trp Gln Gln Met Glu Glu Leu Gly Met Ala
            725                 730                 735

Pro Ala Leu Gln Pro Thr Gln Gly Ala Met Pro Ala Phe Ala Ser Ala
                740                 745                 750

Phe Gln Arg Arg Ala Gly Gly Val Leu Val Ala Ser His Leu Gln Ser
            755                 760                 765

Phe Leu Glu Val Ser Tyr Arg Val Leu Arg His Leu Ala Gln Pro
770                 775                 780

<210> SEQ ID NO 4
<211> LENGTH: 783
<212> TYPE: PRT
<213> ORGANISM: Artificial Sequence
<220> FEATURE:
<223> OTHER INFORMATION: signal peptide of human serum albumin

<400> SEQUENCE: 4

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285
```

```
Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu Ala Pro Thr Tyr Arg Ala Ser Ser Leu Pro Gln Ser Phe Leu Leu
    610                 615                 620

Lys Cys Leu Glu Gln Val Arg Lys Ile Gln Gly Asp Gly Ala Ala Leu
625                 630                 635                 640

Gln Glu His Ile Cys Ala Thr Tyr His Ile Cys His Pro Glu Glu Leu
                645                 650                 655

Val Leu Leu Gly His Ser Leu Gly Ile Pro Trp Ala Pro Leu Ser Ser
            660                 665                 670

Cys Pro Ser Gln Ala Leu Gln Leu Ala Gly Cys Leu Ser Gln Leu His
        675                 680                 685

Ser Gly Leu Phe Leu Tyr Gln Gly Leu Leu Gln Ala Leu Glu Gly Ile
    690                 695                 700
```

```
Ser Pro Glu Leu Gly Pro Thr Leu Asp Thr Leu Gln Leu Asp Val Ala
705                 710                 715                 720

Asp Phe Ala Thr Thr Ile Trp Gln Gln Met Glu Glu Leu Gly Met Ala
                725                 730                 735

Pro Ala Leu Gln Pro Thr Gln Gly Ala Met Pro Ala Phe Ala Ser Ala
            740                 745                 750

Phe Gln Arg Arg Ala Gly Gly Val Leu Val Ala Ser His Leu Gln Ser
        755                 760                 765

Phe Leu Glu Val Ser Tyr Arg Val Leu Arg His Leu Ala Gln Pro
    770                 775                 780

<210> SEQ ID NO 5
<211> LENGTH: 2352
<212> TYPE: DNA
<213> ORGANISM: Artificial Sequence
<220> FEATURE:
<223> OTHER INFORMATION: signal peptide of human serum albumin

<400> SEQUENCE: 5
```

| | | | | | |
|---|---|---|---|---|---|
| atgaagtggg | taacctttat | ttcccttctt | tttctcttta | gctcggctta | ttccagggt      60 |
| gtgtttcgtc | gagatgcaca | caagagtgag | gttgctcatc | ggtttaaaga | tttgggagaa    120 |
| gaaaatttca | agccttggt  | gctgattgcc | tttgctcagt | atcttcagca | gtgtccattt    180 |
| gaagatcatg | taaaattagt | gaatgaagta | actgaatttg | caaaaacatg | tgttgctgat    240 |
| gagtcagctg | aaaattgtga | caaatcactt | catacccttt | ttggagacaa | attatgcaca    300 |
| gttgcaactc | ttcgtgaaac | ctatggtgaa | atggctgact | gctgtgcaaa | acaagaacct    360 |
| gagagaaatg | aatgcttctt | gcaacacaaa | gatgacaacc | caaacctccc | ccgattggtg    420 |
| agaccagagg | ttgatgtgat | gtgcactgct | tttcatgaca | atgaagagac | atttttgaaa    480 |
| aaatacttat | atgaaattgc | cagaagacat | ccttactttt | atgccccgga | actccttttc    540 |
| tttgctaaaa | ggtataaagc | tgcttttaca | gaatgttgcc | aagctgctga | taaagctgcc    600 |
| tgcctgttgc | caaagctcga | tgaacttcgg | gatgaaggga | aggcttcgtc | tgccaaacag    660 |
| agactcaagt | gtgccagtct | ccaaaaattt | ggagaaagag | ctttcaaagc | atgggcagta    720 |
| gctcgcctga | gccagagatt | tcccaaagct | gagttttgcag | aagtttccaa | gttagtgaca    780 |
| gatcttacca | aagtccacac | ggaatgctgc | catggagatc | tgcttgaatg | tgctgatgac    840 |
| agggcggacc | ttgccaagta | tatctgtgaa | aatcaagatt | cgatctccag | taaactgaag    900 |
| gaatgctgtg | aaaaacctct | gttggaaaaa | tcccactgca | ttgccgaagt | ggaaaatgat    960 |
| gagatgcctg | ctgacttgcc | ttcattagct | gctgattttg | ttgaaagtaa | ggatgtttgc   1020 |
| aaaaactatg | ctgaggcaaa | ggatgtcttc | ctgggcatgt | ttttgtatga | atatgcaaga   1080 |
| aggcatcctg | attactctgt | cgtgctgctg | ctgagacttg | ccaagacata | tgaaaccact   1140 |
| ctagagaagt | gctgtgccgc | tgcagatcct | catgaatgct | atgccaaagt | gttcgatgaa   1200 |
| tttaaacctc | ttgtggaaga | gcctcagaat | ttaatcaaac | aaaattgtga | gcttttgag    1260 |
| cagcttggag | agtacaaatt | ccagaatgcg | ctattagttc | gttacaccaa | gaaagtaccc   1320 |
| caagtgtcaa | ctccaactct | tgtagaggtc | tcaagaaacc | taggaaaagt | gggcagcaaa   1380 |
| tgttgtaaac | atcctgaagc | aaaaagaatg | ccctgtgcag | aagactatct | atccgtggtc   1440 |
| ctgaaccagt | tatgtgtgtt | gcatgagaaa | acgccagtaa | gtgacagggt | cactaaatgc   1500 |
| tgcacagaat | ccttggtgaa | caggcgacca | tgcttttcag | ctctggaagt | cgatgaaaca   1560 |
| tacgttccca | aagagtttaa | tgctgaaaca | ttcaccttcc | atgcagatat | atgcacactt   1620 |

```
tctgagaagg agagacaaat caagaaacaa actgcacttg ttgagcttgt gaaacacaag    1680
cccaaggcaa caaagagca actgaaagct gttatggatg atttcgcagc ttttgtagag    1740
aagtgctgca aggctgacga taaggagacc tgctttgccg aggagggtaa aaaacttgtt    1800
gctgcaagtc aagctgcctt aggcttaaca ccattaggcc ctgccagctc cctgccccag    1860
agcttcctgc tcaagtgctt agagcaagtg aggaagatcc agggcgatgg cgcagcgctc    1920
caggagaagc tgtgtgccac ctacaagctg tgccaccccg aggagctggt gctgctcgga    1980
cactctctgg gcatcccctg gctcccctg agcagctgcc ccagccaggc cctgcagctg    2040
gcaggctgct tgagccaact ccatagcggc cttttcctct accaggggct cctgcaggcc    2100
ctggaaggga tctcccccga gttgggtccc accttggaca cactgcagct ggacgtcgcc    2160
gactttgcca ccaccatctg gcagcagatg aagaactgg aatggcccc tgccctgcag    2220 cccacccagg gtgccatgcc ggccttcgcc tctgctttcc agcgccgggc aggaggggtc    2280
ctggttgcct cccatctgca gagcttcctg gaggtgtcgt accgcgttct acgccacctt    2340
gcccagccct ga                                                        2352

<210> SEQ ID NO 6
<211> LENGTH: 2352
<212> TYPE: DNA
<213> ORGANISM: Artificial Sequence
<220> FEATURE:
<223> OTHER INFORMATION: signal peptide of human serum albumin

<400> SEQUENCE: 6
atgaagtggg taacctttat ttccttctt tttctcttta gctcggctta ttccaggggt     60
gtgtttcgtc gagatgcaca caagagtgag gttgctcatc ggtttaaaga tttgggagaa   120
gaaaatttca agccttggt gctgattgcc tttgctcagt atcttcagca gtgtccattt    180
gaagatcatg taaaattagt gaatgaagta actgaatttg caaaaacatg tgttgctgat   240
gagtcagctg aaaattgtga caaatcactt catacccttt ttggagacaa attatgcaca   300
gttgcaactc ttcgtgaaac ctatggtgaa atggctgact gctgtgcaaa acaagaacct   360
gagagaaatg aatgcttctt gcaacacaaa gatgacaacc caaacctccc ccgattggtg   420
agaccagagg ttgatgtgat gtgcactgct tttcatgaca atgaagagac attttttgaaa   480 aaatacttat atgaaattgc cagaagacat ccttactttt atgccccgga actcctttc    540 tttgctaaaa ggtataaagc tgcttttaca gaatgttgcc aagctgctga taaagctgcc    600
tgcctgttgc caaagctcga tgaacttcgg gatgaaggga aggcttcgtc tgccaaacag   660
agactcaagt gtgccagtct ccaaaaattt ggagaaagag ctttcaaagc atgggcagta    720
gctcgcctga ccagagatt tcccaaagct gagtttgcag aagtttccaa gttagtgaca    780
gatcttacca agtccacac ggaatgctgc catggagatc tgcttgaatg tgctgatgac    840
agggcggacc ttgccaagta tatctgtgaa aatcaagatt cgatctccag taaactgaag    900
gaatgctgtg aaaaacctct gttggaaaaa tcccactgca ttgccgaagt ggaaaatgat   960
gagatgcctg ctgacttgcc ttcattagct gctgattttg ttgaaagtaa ggatgttttgc  1020 aaaaactatg ctgaggcaaa ggatgtcttc ctgggcatgt ttttgtatga atatgcaaga   1080
aggcatcctg attactctgt cgtgctgctg ctgagacttg ccaagacata tgaaaccact   1140
ctagagaagt gctgtgccgc tgcagatcct catgaatgct atgccaaagt gttcgatgaa   1200
tttaaacctc ttgtggaaga gcctcagaat ttaatcaaac aaaattgtga gcttttgtgag  1260 cagcttggag agtacaaat ccagaatgcg ctattagttc gttacaccaa gaaagtaccc    1320
```

```
caagtgtcaa ctccaactct tgtagaggtc tcaagaaacc taggaaaagt gggcagcaaa    1380
tgttgtaaac atcctgaagc aaaaagaatg ccctgtgcag aagactatct atccgtggtc    1440
ctgaaccagt tatgtgtgtt gcatgagaaa acgccagtaa gtgacagggt cactaaatgc    1500
tgcacagaat ccttggtgaa caggcgacca tgcttttcag ctctggaagt cgatgaaaca    1560
tacgttccca aagagtttaa tgctgaaaca ttcaccttcc atgcagatat atgcacactt    1620
tctgagaagg agagacaaat caagaaacaa actgcacttg ttgagcttgt gaaacacaag    1680
cccaaggcaa caaaagagca actgaaagct gttatggatg atttcgcagc ttttgtagag    1740
aagtgctgca aggctgacga taaggagacc tgctttgccg aggagggtaa aaaacttgtt    1800
gctgcaagtc aagctgcctt aggcttagca ccaacatacc gtgctagctc cctgccccag    1860
agcttcctgc tcaagtgctt agagcaagtg aggaagatcc agggcgatgg cgcagcgctc    1920
caggagcata tttgtgccac ctaccatatt tgccacccg aggagctggt gctgctcgga    1980
cactctctgg gcatcccctg ggctcccctg agcagctgcc ccagccaggc cctgcagctg    2040
gcaggctgct tgagccaact ccatagcggc cttttcctct accaggggct cctgcaggcc    2100
ctggaaggga tctcccccga gttgggtccc accttggaca cactgcagct ggacgtcgcc    2160
gactttgcca ccaccatctg gcagcagatg gaagaactgg gaatggcccc tgccctgcag    2220
cccacccagg gtgccatgcc ggccttcgcc tctgctttcc agcgccgggc aggaggggtc    2280
ctggttgcct cccatctgca gagcttcctg gaggtgtcgt accgcgttct acgccacctt    2340
gcccagccct ga                                                       2352
```

MUTANT G-CSF FUSION PROTEIN, AND PREPARATION AND USE THEREOF

BACKGROUND OF THE PRESENT INVENTION

1. Field of Invention

The present invention relates to a new fusion protein having the function of accelerating the restoration of granulocytes, a method for preparing the same, a pharmaceutical preparation containing the same, and a use thereof in the field of medicine and especially in treatment of neutropenia or leucopenia.

2. Description of Related Arts

Figure 1:
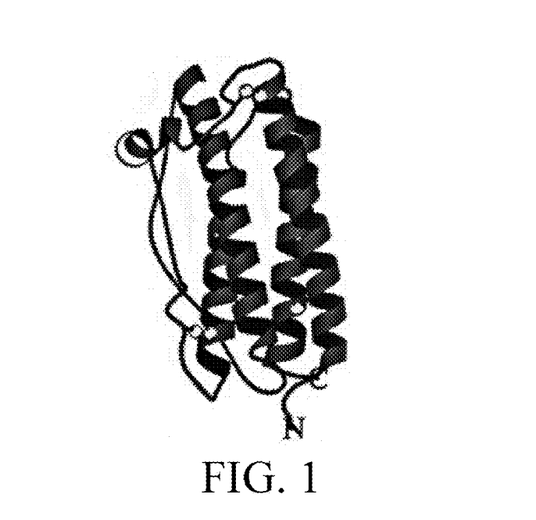
FIG. 1 is a three-dimensional structural model of G-CSF, which includes 4 α-helix regions.

Human granulocyte-colony stimulating factor (G-CSF) is a long polypeptide chain glycoprotein derived from monocytes and fibroblasts, which can induce the proliferation and differentiation of hematopoietic stem cells, promote increase of neutrophilic granulocytes in blood, and also stimulate the release of mature neutrophilic granulocytes from marrow, and activate neutrophilic granulocytes. The main spatial structure of G-CSF is helix with 103 out of 174 residues forming 4 α-helixes, as shown in FIG. 1 (Hill C P et al., Proc Natl Acad Sci USA, 90:5167-5171, 1993). Since 1991, recombinant human granulocyte-colony stimulating factor (rG-CSF) has been widely used in treatment of bone marrow suppression caused by cancer chemotherapy, which can significantly ameliorate the severity and duration of neutropenia elicited by chemotherapy. At present, numerous commercial rG-CSF preparations are available, e.g. filgrastim, which is a generic term with its brand names from various manufacturers, including NEUTROGIN® and GRAN®, lenograstim, which is a generic term with its brand names from various manufacturers, including GRANOCYTE® and NEUTROGIN®, and nartograstim, which is a generic term with its brand name as NEU-UP®. Among them, filgrastim and nartograstim are both non-glycosylated rG-CSF produced in recombinant E. coli cells, and lenograstim is glycosylated rG-CSF expressed in CHO cells.

However, natural or recombinant G-CSF has a quite short circulation half-life of only 2-4 hours in human body because it is prone to clear by filtration due to small molecular weight, and thus in each chemotherapeutic cycle, injection of 1 to 2 times per day for 5-7 consecutive days is required (Welte K et al, Proc Nat Acad Sci USA, 82:1526-1530, 1985; Frampton J E et al, Drugs, 48: 731-760, 1994). Extension of in vivo half-life of a G-CSF preparation can lower the administration times. One route to increase in vivo half-life of G-CSF protein is to decrease in vivo clearance of the protein, including clearance through kidney, degradation by a protease, and receptor-mediated clearance. G-CSF protein may be conjugated to some components able to enhance the apparent molecular weight, so as to slow down the renal clearance rate. Also, attachment of the protein to these components can effectively prevent a protease from contacting the protein, thereby decreasing the rate of degradation by the protease. For some proteins having relatively long half-life in serum, such as albumin and IgG, there is an FcRn-mediated protection effect against endocytosis with the basic mechanism that Fc region of IgG and albumin can bind to a corresponding FcRn receptor on cell surface under normal physiological conditions, and then are endocytosed after binding. Due to the decreased pH in a phagocyte, the bound complex disassociates, IgG and albumin are released from the cells again. IgG and albumin are protected against degradation and metabolism because of the presence of the FcRn-mediated circulation (Junghans R P, Immunol Res., 16:29-57, 1997; Chaudhury C et al, J Exp Med., 197: 315-322, 2003; Chaudhury C et al, Biochemistry., 45:4983-4990, 2006). Therefore, fusion of G-CSF with HAS or with the Fc fragment of IgG could prolong half-life. Recombinant human granulocyte-colony stimulating factor modified with PEG (PEG-rG-CSF, trade name: Neulasta®) can prolong the half-life of G-CSF (Harris J M, Clin Pharmacokinet, 40:539-551, 2001). The rHSA/G-CSF obtained through the albumin fusion technology, that is, through fusion expression of human albumin and G-CSF by genetic engineering, can also increase the in vivo half-life of G-CSF (Wendy Halpern et al, Pharm Res, 19:1720-1729, 2002); similarly, fusion to the Fc fragment of an antibody can also greatly improve the in vivo half-life of G-CSF (Cox George N et al., Experimental Hematology, 32: 441-449, 2004).

But still there've been lots of disadvantages in clinical application for the existing G-CSF which has relatively prolonged half live.

First of all, although the half-life of G-CSF can be prolonged by increasing the molecular weight through modification with PEG or through the albumin fusion technology, the improvement is limited due to the presence of a G-CSF receptor-mediated clearance (RMC) route, as described in more detail as below.

The in vivo clearance of G-CSF is different from that of an ordinary protein drug, in that a G-CSF receptor mediated clearance route exists besides the route such as renal clearance and degradation by a protease. The RMC route refers to that G-CSF (including a modified equivalent thereof) binds to a G-CSF receptor to form a G-CSF/G-CSFR complex, and then the G-CSF/G-CSFR complex is endocytosed by a cell, fused to a lysosome, and degraded by a protease. A key factor affecting the RMC rate is binding of G-CSF to and disassociation of G-CSF from the receptor. This route is a feedback mechanism of regulation of endogenous G-CSF by an organism per se. G-CSFR is highly expressed on the surface of neutrophilic granulocytes, and clearance of G-CSF can be accelerated when the number of neutrophilic granulocytes is increased. Through modification with PEG or through the albumin fusion technology, G-CSF can be protected against degradation by a protease in the circulation system due to increased hydrodynamic radius of G-CSF and thus alleviated renal filtration, thereby extending the in vivo half-life of G-CSF. However, G-CSF is cleared by the G-CSF receptor in the RMC route, and the aforesaid technologies have no obvious influence on the rate of G-CSF binding to and disassociating from the receptor, and thus cannot significantly reduce the clearance rate of RMC. Accordingly, for a modified G-CSF preparation (PEGylated, albumin fusion or other carrier protein fusion manners), the RMC route become the main cleareance route in vivo. In order to obtain a modified G-CSF preparation with a longer half-life and a better therapeutic effect, suppression of the RMC route is required. For example, due to the existence of the RMC effect, the half-life of the rHSA/G-CSF fusion protein reaches only 7. 7-13. 3 hrs even if the renal clearance route is avoided (Wendy Halpern et al, Pharm Res, 19: 1720-1729, 2002), and the half-life is generally as long as 70-80 hrs when albumin is fused to other cytokines (Müller D et al, J Biol Chem, 282: 12650-12660, 2007).

Generally, the receptor-mediated clearance (RMC) is associated with activation of the receptor, and binding of the polypeptide to the receptor thereof in a non-activated state cannot lead to RMC. Clearance is elicited when an activated receptor binds to the polypeptide, and is then endocytosed by a cell and degraded by a lysosome. Bowen et al find through research that the molecular weight of the PEG moiety on the PEG modified G-CSF protein is obviously inversely proportional to the in vitro activity of PEG/G-CSF (Bowen et al, Exp Hematol, 27:425-432, 1999). However, in vivo test results indicate that the in vitro activity of PEG/G-CSF increases with the increase of the molecular weight of the PEG moiety. It is speculated that the low affinity between PEG/G-CSF conjugate and G-CSFR has the effect of enhancing the half-life, because of the receptor mediated endocytosis which is an important mechanism for regulating the level of hematopoietic growth factors. It is further found that if there is amino acid substitution in helix regions of G-CSF, that is, in amino acid residues of amino acids 11-14, 71-95, 102-125, and 145-170, the receptor mediated clearance shall be reduced after the resulting polypeptide is conjugated to PEG (Nissen et al, U.S. Pat. No. 6,831,158).

Currently, a mutant with enhanced half-life is obtained through site-specific substitution on the G-CSF molecules. Based on the recognition that amino acid substitutions could reduce receptor binding affinity in intracellular endosomal compartments, thereby leading to increased recycling in the ligand-sorting process and consequently resulting in longer half-life in extracellular medium, Sarker et al substitute individual amino acid residues in G-CSF with a histidine residue to obtain two G-CSF mutants D110H and D113H with prolonged half-life after screening (Sarker et al, Nature Biotech, 20:908-913, 2002).

Although the fusion protein of G-CSF with albumin or Fc fragment of IgG has a longer half-life, existing technology for extending the half-life through substitution of G-CSF is not necessarily applicable for the G-CSF fusion protein. This is mainly due to that the binding affinity of G-CSF to the receptor is affected after being fused with albumin or Fc. This effect exists for two proteins in the fusion protein, i.e. G-CSF and the fusion carrier. On one hand, the binding between G-CSF and the G-CSF receptor is affected; and on the other hand, the binding between albumin (or Fc) and FcRn is also affected. Both of the changes correlate to the half-life of G-CSF, and thus it is extremely hard to further extend the half-life of the G-CSF fusion protein. However, it is found that a mutated fusion protein obtained by introducing some substitution sites that are currently found to be able to extend the half-life of G-CSF into the rHSA/G-CSF fusion protein according to the existing research can not even prolong the half-life of rHSA/G-CSF fusion protein than those unmutated one (referring to Table 2).

Secondly, there is still a long period of time during which neutrophilic granulocytes are deficient and serious infection risk exists even if G-CSF therapy is given to the patients after chemotherapy. For those patients, it is important to shorten the duration of neutropenia and alleviate the severity as much as possible, thereby minimizing the potential of serious infection. However, a currently used long acting G-CSF preparation can only lower the dosing frequency, yet cannot shorten the duration of neutropenia. Therefore, it shows immense significance to shorten the duration time of neutropenia while extending the half-life for those patients receiving chemotherapy or radiotherapy.

Thirdly, although the existing PEG or albumin modified G-CSF preparations can extend the in vivo half-life of G-CSF, the blockage of the active sites and the steric hindrance effect are always accompanied by the decline of the biological activity. For example, the PEGylated G-CSF only remains 60% of the original activity, and the HAS fused G-CSF only remains 1/7 of the original activity (Fleer et al., U.S. Pat. No. 5,876,969), and thus a large dose of preparation is required to ensure the therapeutic effect in clinical application. Large dosage of preparation of G-CSF therapy leads to side effect of accompanied dose-dependent bone pain. Therefore, the patients anticipate a novel G-CSF preparation that does not cause bone pain in use, or a product that has a in vivo biological activity high enough without causing bone pain while being used at an effective dosage.

Another problem caused by the large dose is increased concentration of the product preparation. For example, the concentration of the PEG/G-CSF preparation Neulasta® is 10 mg/mL, which is 33 times higher than that of the previous G-CSF preparation Filgrastim (0. 3 mg/mL). High concentration of protein preparation can easily result in protein aggregation during transportation and storage. Research results suggest that therapy protein aggregation will increase immunogenicity (De Groot A S and Scott D W, Trends Immunol., 28:482-490, 2007). Recombinant protein polymer activates B cell proliferation by crosslinking B cell receptors, and thus initiates B cell and T cell immunity (Rosenberg A S, AAPS J., 8: 501-507, 2006). Meanwhile, the recombinant protein polymer is easily phagocytized by antigen presenting cells (APCs), therefore accelerating the maturity of the dendritic cells (DCs) and arousing a variety of immune responses (De Groot A S and Scott D W, Trends Immunol., 28:482-490, 2007).

Finally, there is still a long period of time during which neutrophilic granulocytes are deficient and serious infection risk exists even if G-CSF therapy is given to the patients after chemotherapy. However, a currently used long acting G-CSF preparation can only lower the dosing frequency, yet cannot shorten the duration of neutropenia. For those patients, the potential of serious infection can be minimized if the duration of neutropenia can be shortened and the severity is alleviated.

As described above, there is still room for the performance improvement for the G-CSF preparations currently available in the market. Based on the existing technology, development of a novel G-CSF preparation with better therapeutic effect, longer half-life, and higher safety is of great significance. The present invention involves such a novel G-CSF preparation.

SUMMARY OF THE PRESENT INVENTION

The present invention discloses a mutant G-CSF fusion protein having a longer half-life compared with the existing products, and preparation and usage thereof. In addition, it is found unexpectedly by the inventor in in vivo and in vitro tests that the mutant has higher biological activity thus restoring the number of neutrophilic granulocytes more quickly.

In the first aspect, the present invention provides a mutant G-CSF fusion protein, which is a fusion protein having the activity of stimulating the proliferation of neutrophilic granulocytes, and having a basic structure of G-CSF/carrier protein or carrier protein/G-CSF, in which the G-CSF moiety contains one of K34H, L35I, K40H, and L41I substitutions, or a combination thereof. For example, for K34H substitution, the G-CSF moiety may contain K34H substitution alone, or contain a combination of K34H substitution with one or more of L35I, K40H, and L41I substitutions.

Preferably, the G-CSF moiety further contains one of T1A, L3T, G4Y, and P5R substitutions, or a combination thereof.

More preferably, the G-CSF moiety contains K34H, L35I, K40H, L41I, T1A, L3T, G4Y, and P5R substitutions. Preferably, the G-CSF moiety has an amino acid sequence included but not limited to SEQ ID NO: 2.

As mentioned in embodiments of the present invention, in the mutant G-CSF fusion protein in the present invention, compared with SEQ ID NO: 1, the G-CSF may have any one of K34H, L35I, K40H or L41I substitution, or have K34H+L35I, K34H+K40H, K34H+L41I, L35I+K40H, L35I+L41I, or K40H+L41I substitutions, and most preferably, have K34H, L35I, K40H, L41I, T1A, L3T, G4Y, and P5R substitutions.

The G-CSF moiety should have an amino acid sequence that has at least 90% sequence identity with SEQ ID NO: 1. Preferably, the G-CSF moiety has an amino acid sequence that has at least 96% (calculated based on that 7 out of 174 amino acid are mutated) sequence identity with SEQ ID NO: 1.

The carrier protein may be one well known to and commonly used by those skilled in the art, including, but not limited to, human serum albumin, human transferrin, and antibody Fc fragment.

Most preferably, the mutant G-CSF fusion protein has an amino acid sequence shown in SEQ ID NO: 4.

In addition, the carrier protein may be connected to the G-CSF moiety by a linker peptide, for example, some short linker peptides rich in Gly and Ser, such as $(GlyGlyGlyGlySer)_n$, wherein n ranges between 1 and 10, and the peptides that already wildly used in connecting, like the peptides that Daming Shan had mentioned (Shan D et al., J Immunol., 162:6589-6595, 1999).

In the second aspect, the present invention provides a isolated polynucleotide encoding the mutant fusion protein.

The nucleotide sequence encoding the mutant rG-CSF may be prepared by any suitable technologies well known to those skilled in the art, including, but not limited to, recombinant DNA technology and chemical synthesis. Alternatively, the nucleotide sequence having the amino acid sequence of G-CSF shown in SEQ ID NO: 1 may be synthesized first, and then a sequence is inserted, substituted or deleted through side-directed substitution, directed mutagenesis or other technologies well known to those skilled in the art, to obtain the desired nucleotide sequence.

The nucleotide sequence encoding the carrier protein may be prepared by any suitable technologies well known to those skilled in the art. In a specific embodiment of the present invention, the nucleotide sequence of the carrier protein is a nucleotide sequence encoding human serum albumin, or the nucleotide sequence which has at least 95% sequence identity with the nucleotide sequence encoding human serum albumin.

The fusion technology for the nucleotide sequence encoding the mutant rG-CSF and the nucleotide sequence encoding the carrier protein may be made reference to common molecular biology literature, such as "Molecular Cloning: A Laboratory Manual" (J. Sambrook et al., Science Press, 1995).

In the third aspect, the present invention provides an expression vector, which is an expression vector of the polynucleotide sequence described above.

The gene sequence expressing the rHSA/G-CSF fusion protein may be expressed by an expression system well known to those skilled in the art, including, but not limited to, bacteria transformed with a vector such as recombinant bacteriophage and plasmid, yeast transformed with a yeast expression vector, filamentous fungi transformed with a fungi vector, insect cells transfected with a virus vector, and plant cells. In a specific embodiment of the present invention, the expression system is expression in *Pichia pastoris* in the form of excretion. *Pichia pastoris* has the advantages of high level of expression, low cost, and protein processing, folding, and post-translation modification of an eukaryotic expression system. In specific production, the cells may be cultured in a shake flask in laboratory, or cultured through fermentation in a fermenter (including continuous, batch, fed-batch, and solid state fermentation).

In the forth aspect, the present invention provides a recombinant host cell, which are transformed with the expression vectors as described in the third aspect of the present invention, or of which the chromosome is integrated with the foregoing polynucleotide.

The host cell contains an expression vector, and the expression vector contains the isolated polynucleotide molecule encoding the fusion protein as described above. The host cell is cultivated under suitable conditions, so that the host cell expresses the corresponding recombinant fusion protein.

The host cell is an eukaryotic host cell, and may be selected from *Saccharomyces cerevisiae* cells, Hank's yeast, *Pichia pastoris* cells, CHO cells, COS cells, BHK cells, or HEK 293 cells.

In the fifth aspect, the present invention provides an approach to prepare the mutant fusion protein. The process includes synthesizing a nucleotide sequence able to express the mutant fusion protein, inserting the nucleotide sequence into an expression vector, then transforming a host cell with the expression vector containing the fusion protein gene sequence to induce expression, and preparing the fusion protein through affinity chromatography, ion exchange chromatography and hydrophobic interaction chromatography.

The rHSA/G-CSF fusion protein excreted to the culture medium may be purified by a method well known to those skilled in the art, including, but not limited to, ultrafiltration, ammonium sulfate precipitation, acetone precipitation, ion exchange chromatography, hydrophobic interaction chromatography, reverse phase chromatography, and molecular sieve chromatography. In a specific embodiment of the present invention, the fusion protein is purified to uniform by the inventor via a three-step chromatography means of affinity chromatography, hydrophobic interaction chromatography, and ion exchange chromatography in combination.

In the sixth aspect, the present invention provides a pharmaceutical composition, which contains the mutant G-CSF fusion protein and at least a pharmaceutically acceptable carrier or excipient.

Therapeutically inactive inorganic or organic carrier known to those skilled in the art includes, but is not limited to, lactose, corn starch or a derivative thereof, talc, vegetable oil, wax, fat, a polyhydric compound such as polyethylene glycol, water, sucrose, ethanol, glycerol, and so on. Various preservatives, lubricants, dispersing agents, flavoring agents, moisturizing agents, antioxidants, sweeteners, colorants, stabilizers, salts, buffers, and so on may also be added, and these substances may be used to assist in stabilization of the formulation or improvement of the activity or bioavailability as desired.

The pharmaceutical composition of the present invention may be formulated in liquid, gel, lyophilized or other forms, according to a technology well known to those skilled in the art, to give a drug that is stable for storage and suitable for administration to human or animals.

In the seventh aspect, the present invention discloses a use of the mutant G-CSF fusion protein in preparation of drugs for treating neutropenia or leukopenia.

The fusion protein of the present invention is useful in preparation of drugs for treating diseases, and is especially useful in prevention of infection of cancer patients receiving chemotherapy, radiotherapy, and bone marrow transplant, in treatment of patients having leucopenia and neutropenia, in treatment of patients having acute myeloid leukemia, and in treatment of AIDS or other immunodeficiency diseases. In an embodiment of the present invention, the fusion protein of the present invention is used for treating leucopenia and neutropenia.

In an eighth aspect, the present invention discloses a method for treating neutropenia in mammalians, including injecting therapeutically effective dose of the mutant fusion protein, to accelerate restoration of normal levels of neutrophils in individuals.

The proteins of the present invention may be used alone or in combination, or used in combination with other therapeutic agent.

The therapeutically effective dose, i.e., a dose that is sufficient for bringing an desired effect to the targeted disease, is administrated to the subject. Depending on the specific disease, an accurate dose may be determined by those skilled in the art according to the clinical results, and is preferably 1 µg-1 mg/kg, and more preferably 50-500 µg/kg. In an embodiment of the present invention, the effective dose of the administrated fusion protein refers to a dose that is sufficient for restoration of normal levels of leukocytes and especially neutrophilic granulocytes in a test subject.

The researcher of the present invention constructs numerous rHSA/G-CSF mutants (see Tables 1 and 2), which are expressed in *Pichia pastoris*. For the obtained mutants, ligand-receptor affinity screening test, and biological activity test at cellular level are conducted. An rHSA/mG-CSF mutant fusion protein that binds to the G-CSF receptor with a low affinity is obtained. Compared with the existing products, the mutant fusion protein has a longer half-life. Surprisingly, the mutated fusion protein has a much higher in vivo activity, and thus accelerated restoration of normal levels of neutrophils in individual with even lower side effects than those existing G-CSF fusion proteins. In the research on improvement of the half-life of the G-CSF fusion protein through suppression of the RMC route, a mutated protein able to accelerate the restoration of neutrophilic granulocytes is unexpectedly obtained. This is unexpected and cannot be satisfactorily interpreted by the current research, and further research is needed. However, such an unexpected result is of great significance for the patients receiving chemotherapy or radiotherapy.

SEQUENCE STATEMENT

| SEQ ID NO: | STATEMENT |
|---|---|
| 1 | Amino acid sequence of G-CSF |
| 2 | Amino acid sequence of mutant G-CSF |
| 3 | Amino acid sequence of rHSA/G-CSF fusion protein |
| 4 | Amino acid sequence of rHSA/mG-CSF fusion protein |
| 5 | Complementary DNA sequence that encodes rHSA/G-CSF fusion protein |
| 6 | Complementary DNA sequence that encodes rHSA/mG-CSF fusion protein |

DETAILED DESCRIPTION OF THE PREFERRED EMBODIMENTS

The following definitions are used herein.

G-CSF: human granulocyte-colony stimulating factor; mG-CSF: mutant human granulocyte-colony stimulating factor; HSA: human serum albumin; PEG: polyethylene glycol; rHSA/G-CSF: recombinant human serum albumin-granulocyte-colony stimulating factor; rHSA/mG-CSF: recombinant human serum albumin-mutant granulocyte-colony stimulating factor.

Abbreviations for defining amino acid residue substitution are described with examples below. K34 refers to that a lysine residue is present at position No. 34 of the amino acid sequence; K34H refers to that the lysine residue at position No. 34 is substituted by a histidine residue; and K34H+K40H refers to that the lysine residue at position No. 34 is substituted by a histidine residue and a ysine residue at position No. 40 is substituted by a histidine residue.

The present invention is further described with reference to specific embodiments. It should be understood that the embodiments are only used to illustrate the present invention, instead of limiting the scope of the present invention. In the following embodiments, methods in which specific conditions are not noted are generally carried out under conventional conditions, or under conditions recommended by the manufacturers.

Embodiment 1

Screening of Mutated Sites

Numerous related amino acid residues located on the G-CSF receptor binding interface were mutated, to construct numerous rHSA/G-CSF mutants, in which except for the sequence differences, the mutants were constructed using the same method as that in Embodiment 2. The mutants were expressed in *Pichia pastoris* (the expression and purification method were as described in Embodiments 3-5); and for the obtained mutants, the ligand-receptor affinity was determined by using surface plasma resonance (SPR) technology, and a biological activity test at cellular level was conducted. Through the SPR technology, an association rate constant and a disassociation rate constant were obtained, and thus a ligand-receptor equilibrium disassociation constant was directly determined. The larger the equilibrium disassociation constant was, the lower the ligand-receptor affinity was (Zhou et al, Biochemistry, 32:8193-8198, 1993; Faegerstram and Osh annessy, In handbook of Affinity Chromatography, Marcel Dekker INc, NY, 1993). In Embodiment 8 of the present invention, the method for determining the binding affinity of rHSA/G-CSF to G-CSFR through the SPR technology was described in detail. In Embodiment 7 of the present invention, the method for determining the in vitro biological activity of the mutants was described in detail. The test results of 38 rHSA/mG-CSF mutants are shown in Table 1.

TABLE 1

| | Equilibrium disassociation constant $K_D$ (nmol/L) | in vitro biological activity % (molar ratio) | | Equilibrium disassociation constant $K_D$ (nmol/L) | in vitro biological activity % (molar ratio) |
|---|---|---|---|---|---|
| G-CSF | 0.3 | 100 | A37G | 7.4 | 16 |
| rHSA/G-CSF | 1.3 | 15.6 | T38S | 6.7 | 15 |
| T1A | 1.7 | 30 | K40H | 25.2 | 14 |
| P2K | 1.2 | 12 | L41I | 17.1 | 12 |
| L3T | 1.8 | 40 | H43R | 4.3 | 3.8 |
| G4Y | 1.1 | 38 | P44K | 1.6 | 18 |
| P5R | 1.5 | 44 | E45D | 0.8 | 15 |
| A6G | 8.9 | 11 | E46D | 8.5 | 16 |
| S7T | 1.6 | 12 | Q70K | 5.9 | 17 |
| P10K | 0.9 | 11 | Q90K | 6.8 | 17 |
| Q11N | 3.4 | 11 | L108I | 7.2 | 6.1 |
| S12T | 1.1 | 17 | D109E | 6.5 | 12 |
| L15I | 4.8 | 15 | D112E | 3.1 | 1.3 |
| K16H | 7.3 | 17 | T115S | 2.5 | 12 |
| C17S | 1.3 | 16 | T116S | 2.5 | 17 |
| L19I | 11.2 | 5.6 | Q119N | 1.8 | 13 |
| Q20N | 97.5 | 1.2 | Q120K | 1.5 | 15 |
| K34H | 18.4 | 18 | E123D | 1.5 | 14 |
| L35I | 12.5 | 11 | L124I | 1.4 | 16 |

* rHSA/G-CSF: prepared according to the method in Example 2-4

It can be seen from the test results that compared with rHSA/G-CSF, the substitution in the sites of K34H, L35I, K40H, and L41I, result in higher equilibrium disassociation constant. However, the activity is not obviously improved, indicating that the binding affinity of the mutants to the receptor is low. In contrast, the substitution in the sites of T1A, L3T, G4Y, and P5R could result in higher the activity yet little impact on binding affinity.

According to the above test results, some combinations of mutated sites were re-designed, including K34H+L35I, K34H+K40H, K34H+L41I, L35I+K40H, L35I+L41I, and K40H+L41I. The mutants were obtained following the method above, a second round of optimization and screening tests were carried out following the method above, the in vitro activity was determined following the method described in Embodiment 7, and the in vivo half-life was determined following the method described in Embodiment 9. The results are shown in Table 2. Furthermore, site substitutions of D110H and D113H that are reported to be able to extend the in vivo half-life of G-CSF (Sarker et al., Nature Biotech, 20:908-913, 2002) are introduced as control. In this embodiment, G-CSF is free of N-terminal Met, and D109H and D112H are corresponding to the site substitutions D110H and D113H.

TABLE 2

| Sample | Equilibrium disassociation constant $K_D$ (nmol/L) | in vitro biological activity (%) | half-life (hour) |
|---|---|---|---|
| G-CSF | 0.3 | 100 | 2.8 |
| rHSA/G-CSF | 1.3 | 16 | 8.5 |
| K34H + L35I | 42.7 | 18 | 12.6 |
| K34H + K40H | 40.1 | 12 | 18.0 |
| K34H + L41I | 28.5 | 17 | 13.2 |
| L35I + K40H | 25.5 | 17 | 21.9 |
| L35I + L41I | 23.5 | 13 | 16.7 |
| K40H + L41I | 30.6 | 15 | 24.5 |
| D109H + D112H | 5.3 | 13 | 8.8 |

It can be seen from the above results that compared with rHSA/G-CSF, those mutants have longer half-life, lower binding affinity with the receptor and improved in vivo biological activity. In contrast, when the substitutions (D109H and D112H) able to extend the half-life of G-CSF monomer are applied to the HAS fusion protein, the half-life is not obviously extended.

Embodiment 2

Construction of Yeast Expression Strain of rHSA/G-CSF and Mutant rHSA/mG-CSF

On the basis of the research in Embodiment 1, the mutants were further optimized, and finally an optimized strain having a low affinity to the receptor, a long half-life, and a high activity was screened. In the strain, site substitutions T1A, L3T, G4Y, P5R, K34H, L35I, K40H, and L41I occurred. The strain was constructed as follows.

The DNA sequences encoding HSA/G-CSF (see SEQ NO:5) and HSA/mG-CSF (see SEQ NO: 6) were synthesized by Invitrogen (Shanghai) Corporation, and then inserted into pMD18-T(TaKaRa), to construct plasmids HSA/G-CSF/pMD18-T and HSA/mG-CSF/pMD18-T. HAS carried a natural signal peptide sequence, before which a BamHI site was added, and an EcoRI site was added at 3' end of G-SCF.

Plasmids HSA/G-CSF/pMD18-T and HSA/mG-CSF/pMD18-T were double digested with BamHI/EcoRI, to respectively isolate HSA/G-CSF and HSA/mG-CSF fragments, which were respectively attached to the pPIC9 plasmid digested with the same enzyme, and then used to transform into E. coli DH5a competent cells. The transformants were finally picked into LB liquid medium containing 50 μg/ml ampicillin, and cultured at 37° C. overnight, till monoclonal plaques were grown. Plasmids were then extracted from the transformed plaque by using a conventional method, and double digested with BamHI/EcoRI for identification, and the positive clone having a target sized fragment was sent to Invitrogen Corporation for confirmation by DNA sequencing.

Plasmid that was confirmed by sequencing was linearized by digestion with SalI, transformed into the expression strain GS115 cells by electroporation. Cells were spread on the PDB screening plates (containing 1 M sorbitol, 2% glucose, 1. 34% YNB, $4 \times 10^{-5}$% biotin, and 0. 005% amino acid (free of histidine)) and cultured at 30° C. for 3 days to yield single colonies.

Embodiment 3

Screening of rHSA/G-CSF and Mutant rHSA/mG-CSF

The single colony of recombinant yeasts transformed in Embodiment 2 was grown in the 10 ml BMGY medium (1% yeast extract, 2% peptone, 100 mM potassium phosphate, pH 6.0, 1.34% YNB, 4×10$^{-5}$% biotin, and 1% glycerin), incubated in a shaking incubator (250 rpm) for 24 hrs at 30° C., decant the supernatant after overnight. The supernatant was discarded, 10 ml of BMMY liquid culture medium (1% yeast extract, 2% peptone, 100 mM potassium phosphate, pH 6.0, 1.34% YNB, 4×10$^{-5}$% biotin, and 1% methanol) containing 1% methanol was added, and induced for 72 hrs at 30° C. at 250 rpm, during which methanol was supplemented once every 24 hrs. Starting from time 0, 1 ml of induced yeast solution was sampled every 10 hrs, added into a 1.5 ml centrifuge tube, and centrifuged for 5 min at 5000 g. 10 µl 5× Loading buffer was added into 40 µl of the supernatant, heated in a boiling water bath for 5 min, and analyzed by 12% SDS-PAGE. The expression was analyzed with a control that was induced for 72 hrs with GS115 empty vector strain as a reference.

Embodiment 4

Expression of rHSA/G-CSF and Mutant rHSA/mG-CSF in Yeast

A single colony containing rHSA/G-CSF and mutant recombinant rHSA/mG-CSF obtained in Embodiment 3 was inoculated in the BMGY medium, and incubated overnight at 30° C. in a shaking incubator. When $A_{600}$ was about 5.0, the bacterial were separated through centrifugation, then resuspended in the BMMY medium until $A_{600}$ 2.0, and induced with methanol being added every 24 h to a final concentration of 2% for expression. After 72 h, the supernatant was collected through centrifugation.

The expression level of the fusion protein produced in *Pichia pastoris* was quantified by using a commercially available G-CSF ELISA reagent (Quantikine Human G-CSF Immunoassay, R&D system Cat No. DCS50). The expression level being quantified as about 200 mg/L.

Embodiment 5

Purification of rHSA/mG-CSF from Yeast Fermentation Supernatant of Yeast

Figure 2:
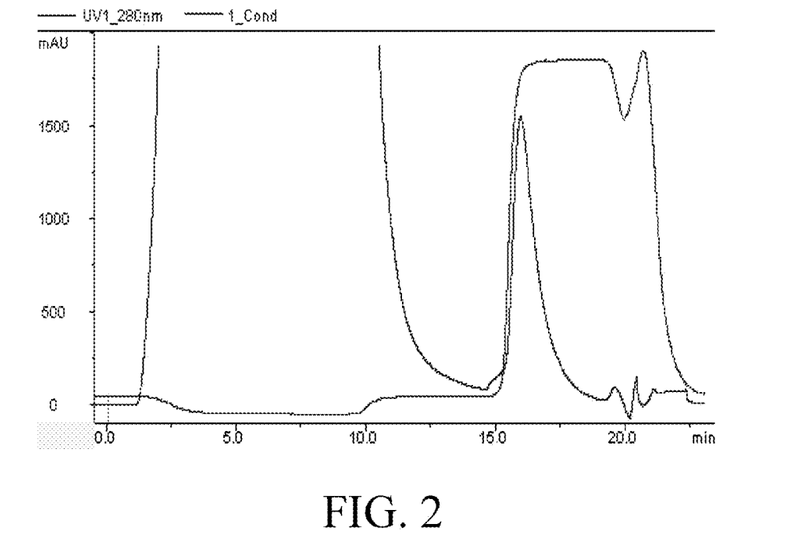
FIG. 2 is an dye affinity chromatogram of rHSA/mG-CSF.

The supernatant of yeast for expression in Embodiment 4 was centrifuged, and the centrifuged supernatant was loaded onto a Blue Sepharose CL6B affinity chromatography column pre-equilibrated with an equilibrium buffer (20 mM, PH 7.0). After loading, the column was washed with 2 column volumes of equilibrium buffer to elute the unbound protein and then the target protein was eluted with an elution buffer (FIG. 2).

Figure 3:
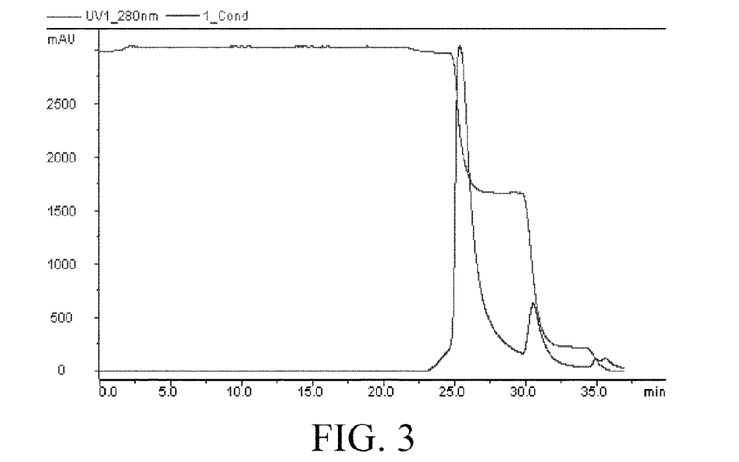
FIG. 3 is a hydrophobic interaction chromatogram of rHSA/mG-CSF.

20 mL of Phenyl High Sub hydrophobic gel was loaded in an XK26/20 column (GE Healthcare Company) with the mobile phase A of aqueous solution containing 20 mM PH 7.0 plus 1 mol/L $(NH_4)_2SO_4$, and the mobile phase B of aqueous solution containing 20 mM PB buffer pH 7.0. To the target peak collected in the above affinity chromatography, ammonium sulfate was supplemented till the final concentration of ammonium sulfate was 1 M, and the resulting solution was loaded on the above chromatography column pre-equilibrated with the mobile phase A. After loading, the column was equilibrated with 2 column volumes of mobile phase A, and then washed with 50% mobile phase B to collect the target peak (FIG. 3).

Figure 4:
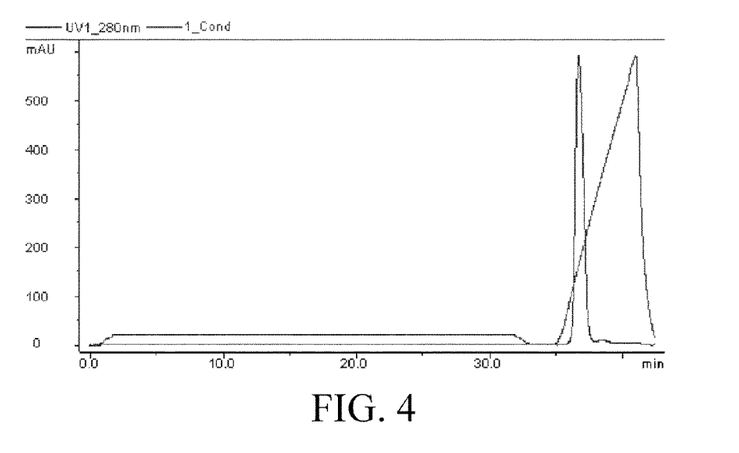
FIG. 4 is an ion exchange chromatogram of rHSA/mG-CSF.

10 mL of Sepharose Q FF gel was loaded in an XK16/20 (GE Healthcare Company) with the mobile phase A of aqueous solution containing 20 mM, PH 7.0, and the mobile phase B of aqueous solution containing 20 mM 0.5 M NaCl, pH 7.0. The eluted peak in the above hydrophobic interaction chromatography was 2-fold diluted with pure water, and then loaded onto the above chromatography column equilibrited with the mobile phase A. After loading, the column was equilibrated with 2 column volume of the mobile phase A, and then linear gradient elution with 10 column volume of 0-100% mobile phase B was performed to collect the target elution peak (FIG. 4).

Embodiment 6

Identification and Quantification of rHSA/mG-CSF

Object: rHSA/mG-CSF obtained through purification in Embodiment 5.

1. Protein concentration was determined by Bradford method.

2. Sodium dodecyl sulfate-polyacrylamide gel electrophoresis (SDS-PAGE)

Figure 5:
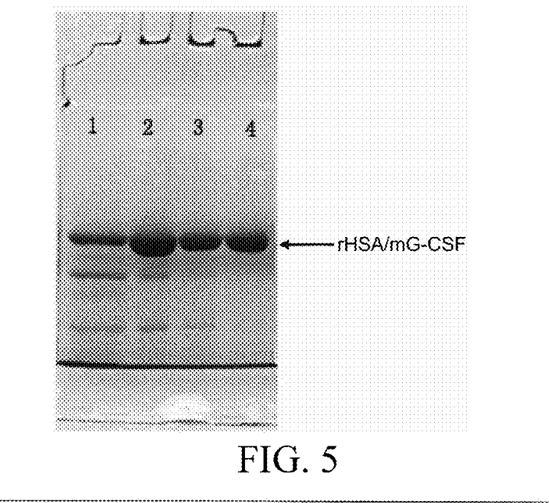
FIG. 5 is an SDS-PAGE of an rHSA/mG-CSF intermediate and the finished product.

The purified of rHSA/mG-CSF was analyzed by 12% SDS-PAGE, showing a single band with a molecular weight of 85 KD (FIG. 5).

3. Size exclusion chromatography—high-performance liquid chromatography (SEC-HPLC)

Figure 6:
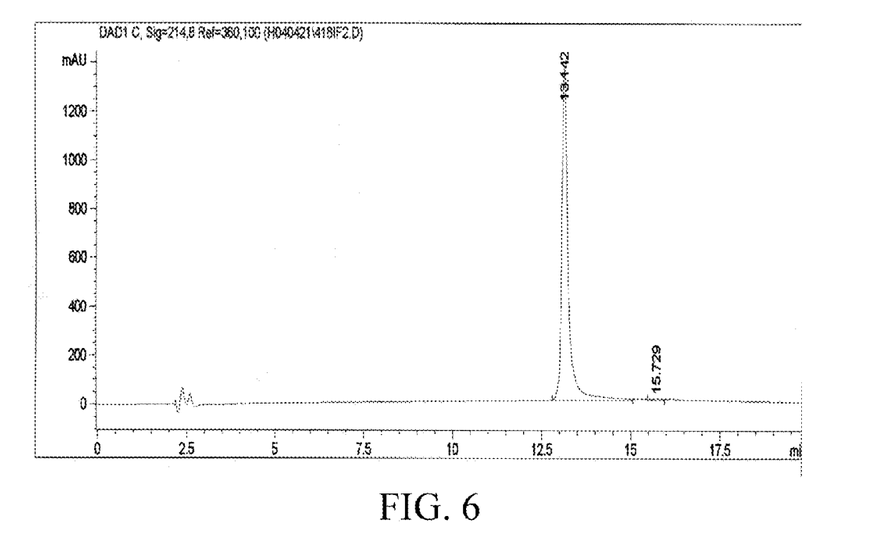
FIG. 6 is a size exclusion chromatogram of rHSA/mG-CSF, in which the purity of the purified rHSA/mG-CSF is 95% or higher.

The result of SEC-HPLC on TSK Gel G3000 Swxl column with 50 mM PB, 0.25M NaCl, pH7.0 was shown in FIG. 5, showing the apparent molecular weight of about 85 KD. (FIG. 6)

4. Reversed-phase chromatography—high-performance liquid chromatography (RP-HPLC)

RP-HPLC was applied on VYDAC protein C4 TP5415 column with the mobile phase A of aqueous solution containing 0.1% TFA in water and mobile phase B of 90% acetonitrile solution containing 0.1% TFA. The result was shown that the purity of the purified rHSA/mG-CSF is 98%.

5. Analysis of amino acid sequencing

The composition of the protein can be more accurately determined through amino acid sequencing. N-terminal and C-terminal amino acid sequencing of the purified rHSA/mG-CSF suggests that the amino acid sequence determined through experiment is consistent with expected result.

Embodiment 7

Determination of In Vitro Biological Activity of rHSA/mG-CSF

Object: rHSA/mG-CSF obtained through purification in Embodiment 5

In vitro bioactivity of the rHSA/mG-CSF was measured in G-CSF-dependent cell line NFS60 by MTT assay (Chinese Pharmacopoeia, 2005 edition, three sections).

1. Preparation of Standard Solution

Standard (manufactured by National Instisutes for Food and Drug Control, lot number: 98/01) for determining the biological activity of recombinant human granulocyte-colony stimulating factor was reconstituted following instruction, and diluted with a basic medium to 50-100 IU per milliliter. In 96 well microplates, a series of 2-fold dilutions were made, to give a total of 8 dilutions, and 2 wells were used for each dilution. 50 µl of standard solution was kept in each well respectively, and surplus solution in the well was discarded.

2. Preparation of Test Solution

The specified amount of the test product was dissolved, and then diluted with a basic medium to 50-100 IU per milliliter. In 96 well microplates, a series of 2-fold dilutions were made, to give a total of 8 dilutions, and 2 wells were used for each dilution. 50 µl of standard solution was kept in each well respectively, and surplus solution in the well was discarded.

3. Determination

Figure 7:
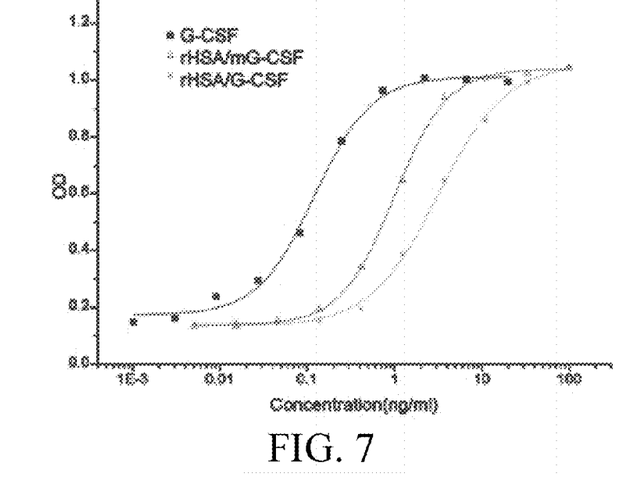
FIG. 7 shows in vitro biological activity analysis of G-CSF, rHSA/G-CSF, and rHSA/mG-CSF.

NFS 60 cell line was cultured in a complete medium at 37° C. in 5% $CO_2$, the cells was controlled to be in a concentration of $1\times10^5$-$4\times10^5$ cells/ml, and then determined after continuous passage culture for 24-36 hrs. Cells were harvested through centrifugation from a sufficient amount of NFS 60 cell culture, washed twice with RPMI 1640 medium, and then re-suspended in a basic medium (900 ml of RPMI 1640+100 ml of new-born calf serum) to formulate a cell suspension containing $2\times10^5$ cells per milliliter. To each well of the 96-well plate containing the standard and the test product, 50 µl of the cell suspension was added, and incubated for 40-48 hrs at 37° C. in 5% $CO_2$. 20 µl of the MTT solution was added to each well, and incubated for 5 hrs at 37° C. in 5% $CO_2$. 100 µl of a lysis buffer was added to each well, and incubated overnight at 37° C. The absorbency at 570 nm was measured using an ELISA microplate reader, with a reference wavelength being 630 nm. A typical activity test result is shown in FIG. 7, and the activity is 48% of that of natural G-CSF. The test data was processed by using Software ORIGIN 7.0 (Microcal Inc.) or through 4-parameter regression calculation, and calculated by a formula below:

$$\text{Biological activity of text product} = Pr \times \frac{Ds \times Es}{Dr \times Er}$$

where Pr is the biological activity of the standard, IU/ml; Ds is a pre-dilution factor of the test product; Dr is a pre-dilution factor of the standard; Es is a dilution factor of the test product equivalent to median effective concentration of the standard; and Er is a dilution factor of the standard at median effective concentration.

Embodiment 8

Determination of Ligand-Receptor Association-Disassociation Constant for the Binding Affinity of rHSA/mG-CSF and Receptor 1. Coupling of G-CSFR The receptor G-CSFR(R&D company, Item No. 381GR/CF) was coupled to $FC_4$ cell of a CM5 chip by using an amine coupling method in Biacore 3000 control software Wizard. HBS-P buffer (10 mM HEPES, 150 mM NaCl, and 0.005% (v/v) surfactant P20, pH 7. 4) was used as the working buffer, and 1 mg/mL of G-CSFR was diluted with 10 mM NaAC (pH 4.5) to a final concentration of 20 µg/mL. A 1:1 mixture of 0.2 M EDC and 50 mM NHS was injected by flowing through the surface of the chip at a rate of 10 µL/min, G-CSFR solution was injected, then 1 M ethanolamine (pH 8.5) was injected for 7 min to block the activated chip surface.

2. Determination of Binding Activity of Ligand to Receptor by Using Surface Plasma Resonance (SPR) Method rHSA/mG-CSF and G-CSF standards were quantitatively diluted with a HBS-P buffer, and a kinetic test was conducted following a kinetic analysis Wizard in Biacore 3000 control software. All the samples were injected at the flow rate of 30 µL/min, and the injection time of 3 min. After 5 min of disassociation, 50 mM NaOH, 1 M NaCL, and HBS-P buffer were respectively injected for 15 s and 60 s at a flow rate of 100 µL/min for regeneration. The obtained data was fitted using a 1:1 Langmuir binding model in Biacore 3000 analysis software, to obtain exact kinetic constants:

the association rate constant $k_a$ and the disassociation rate constant $k_d$, and then the equilibrium disassociation constant was calculated: $K_D = k_d/k_a$. The equilibrium disassociation constant of rHSA/mG-CSF obtained through purification in Embodiment 5 was finally determined to be 42. 6 nm/L.

Embodiment 9

In Vivo Half-Life Test of rHSA/G-CSF and rHSA/mG-CSF

Figure 8:
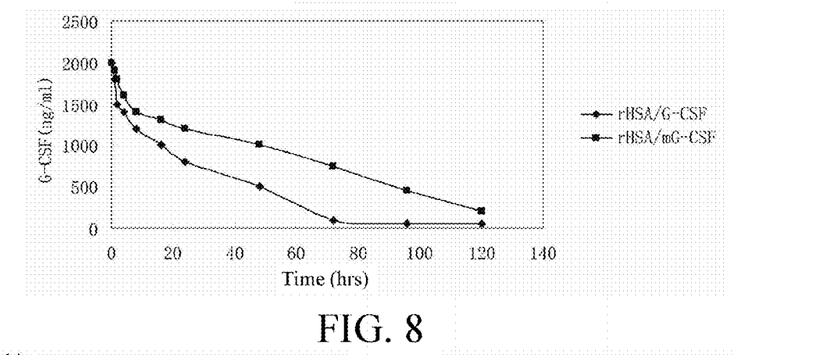
FIG. 8 shows pharmacokinetic research results of rHSA/G-CSF and rHSA/mG-CSF in normal adult SD rats.

Male Sprague Dawley rats were weighed at the day of dosing (280-310 g each), rHSA/G-CSF and rHSA/mG-CSF samples were injected to 3 rats at tail vein at a dose of 100 µg/kg body weight, and blood samples were taken at 30 min, and 1, 2, 4, 8, 24, 48, 72, 96, and 120 hours after injection. After the blood sample was stored at room temperature for 1.5 hrs, serum was separated through centrifugation, and stored at −80° C. Blood agent concentration of rHSA/G-CSF and rHSA/mG-CSF in the sample was measured by using double-antibody sandwich ELISA, and specific operations might be made reference to the operation manual of Human G-CSF DuoSet kit Human G-CSF ELISA Construction Kit (ANTIGENIX). A standard curve was plotted with the obtained data of the standard by using a 4-parameter logistic curve in MicroCal Origin Software, and a regression equation and related statistical parameters were obtained. The data of the sample was inputted into the regression equation of the standard curve by using the Microsoft Excel 2003 Software to calculated related values, which were then plotted. The results are shown in FIG. 8, the half-life of the unmutated rHSA/G-CSF and the mutated rHSA/mG-CSF (obtained in Embodiment 5) is determined respectively to 8.5 hrs and 25.5 hrs, suggesting that the introduction of new amino acid substitutions to G-CSF resulting in obvious in vivo half-life increase.

Embodiment 10

Analysis of In Vivo Biological Activity of rHSA/G-CSF and rHSA/mG-CSF

Figure 9:
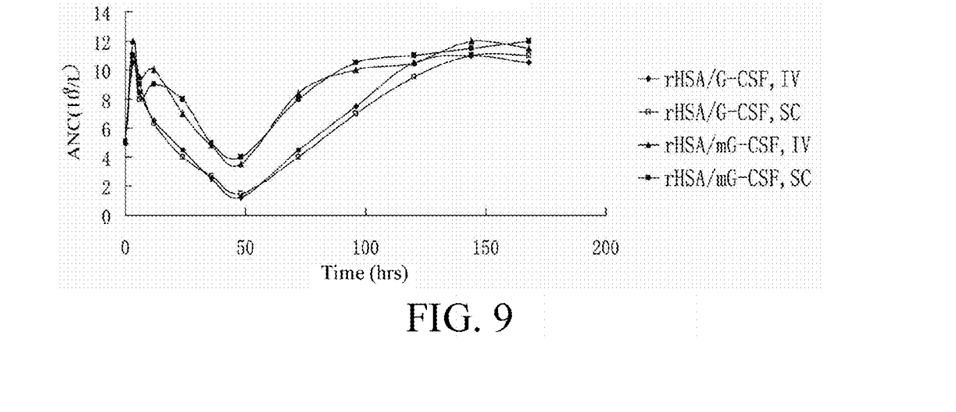
FIG. 9 shows in vivo biological activity analysis of rHSA/G-CSF and rHSA/mG-CSF.

The SPF Sprague Dawley rats (approximately 250-270 g) were divided into several groups each of which has 6 rats. At 24 hours before dosing, 50 mg/kg of cyclophosphamide (CPA) was intraperitoneally injected to each rat. At the day of dosing, the rHSA/G-CSF and rHSA/mG-CSF samples were respectively intravenously or subcutaneously injected to 6 rats that were randomly allocated at a dose of 100 µg/kg body weight. Before dosing and at 6, 12, 24, 36, 48, 72, 96, 120, 144 and 168 hrs after dosing, 300 µl of blood sample was collected from the caudal veins of rats, which was stabilized by adding EDTA. The number of white blood cells in the serum sample were counted. The results are shown in FIG. 9, the number of white blood cells increased significantly after 3 hours counting from the injection of rHSA/G-CSF and rHSA/mG-CSF, and then the number of white blood cells declines due to chemotherapy, and reaches to a minimum at about 48 hours, in which the decline level of white blood cell numberin the rHSA/mG-CSF administrated group is obviously lower than that in the control rHSA/G-CSF group. At about 48 hrs after administration, the number of white blood cell in the rats that are administrated by rHSA/mG-CSF restore to a normal level. In contrast, the number of neutrophilic granulocytes in the rats that are dosed the control rHSA/G-CSF begins to approach the normal level after 72 hrs. Compared with the control group, the duration of leucopenia in the rHSA/mG-CSF administrated group is greatly shortened.

All the literatures mentioned in the present invention were cited in this application as references, just as each one is a separate reference to literature. Besides, after reading the contents described above of the present invention, it should be understood that all the changes, modifications or other equivalent forms of the invention made by technicians in this area are ranged in the claims attached to the application.

What is claimed is:

1. A mutant G-CSF fusion protein, comprising a G-CSF moiety and a carrier protein; said G-CSF moiety being derived from a human G-CSF protein with its amino acid sequence set forth in SEP ID NO: 1; said G-CSF moiety comprising at least one of the mutations of K34H, L35I, K40H and L41I; and said mutant G-CSF fusion protein stimulating proliferations of neutrophilic granulocytes.

2. The mutant G-CSF fusion protein as described in claim 1, wherein the G-CSF moiety has at least 90% sequence identity with SEQ ID NO: 1; and the carrier protein is human serum albumin, human transferrin, or antibody Fc fragment.

3. An isolated polynucleotide molecule encoding the mutant G-CSF fusion protein of claim 1.

4. An expression vector containing the isolated polynucleotide molecule of claim 3.

5. A recombinant host cell comprising the expression vector of claim 4.

6. A method of making the mutant G-CSF fusion protein comprising culturing the host cell of claim 5, and purifying the fusion protein through affinity chromatography, ion exchange chromatography and hydrophobic interaction chromatography.

7. A pharmaceutical composition comprising the mutant G-CSF fusion protein of claim 1 and at least a pharmaceutically acceptable carrier or excipient.

8. A method for treating neutropenia in mammalians, comprising administrating an effective amount of the mutant G-CSF fusion protein of claim 1.

9. The mutant G-CSF fusion protein as described in claim 1, wherein the G-CSF moiety further comprises one or more substitutions of T1A, L3T, G4Y and P5R.

10. The mutant G-CSF fusion protein as described in claim 9, wherein the G-CSF moiety has at least 90% sequence identity with SEQ ID NO: 1.

11. The mutant G-CSF fusion protein as described in claim 9, wherein the G-CSF moiety further comprises one or more substitutions of K34H, L35I, K40H, L41I, T1A, L3T, G4Y and P5R.

12. The mutant G-CSF fusion protein as described in claim 11, wherein the G-CSF moiety has at least 90% sequence identity with SEQ ID NO: 1; and the carrier protein is human serum albumin, human transferrin, or antibody Fc fragment.

13. The mutant G-CSF fusion protein as described in claim 11, wherein the G-CSF moiety comprises the amino acid sequence as set forth in SEQ ID NO: 2.

14. The mutant G-CSF fusion protein as described in claim 13, wherein the G-CSF moiety has at least 90% sequence identity with SEQ ID NO: 1; and the carrier protein is human serum albumin, human transferrin, or antibody Fc fragment.

15. The mutant G-CSF fusion protein as described in claim 11, wherein the mutant G-CSF fusion protein comprises the sequence set forth in SEQ ID NO: 4.

16. The mutant G-CSF fusion protein as described in claim 15, wherein the G-CSF moiety has at least 90% sequence identity with SEQ ID NO: 1; and the carrier protein is human serum albumin, human transferrin, or antibody Fc fragment.

\* \* \* \* \*